United States Patent [19]

Siren

[11] Patent Number: 5,342,832
[45] Date of Patent: * Aug. 30, 1994

[54] USE OF MONO AND DI INOSITOLPHOSPHATES FOR TREATING INFLAMMATION

[75] Inventor: Matti Siren, Helsinki, Finland

[73] Assignee: Perstorp AB, Perstorp, Sweden

[*] Notice: The portion of the term of this patent subsequent to May 21, 2008 has been disclaimed.

[21] Appl. No.: 862,564

[22] PCT Filed: Dec. 18, 1990

[86] PCT No.: PCT/SE90/00842
§ 371 Date: Aug. 21, 1992
§ 102(e) Date: Aug. 21, 1992

[87] PCT Pub. No.: WO91/09601
PCT Pub. Date: Jul. 11, 1991

[30] Foreign Application Priority Data

Dec. 21, 1989 [SE] Sweden ................ 8904355

[51] Int. Cl.$^5$ .............................. A61K 31/66
[52] U.S. Cl. ................ 514/103; 514/109; 514/129
[58] Field of Search .............. 514/129, 109, 103

[56] References Cited

U.S. PATENT DOCUMENTS 4,562,449  3/1987  Ropars et al. ............... 424/1
5,019,566  5/1991  Siren ........................ 514/103

FOREIGN PATENT DOCUMENTS 0262227   3/1987   European Pat. Off. .
WO 8900156 1/1989  PCT Int'l Appl. .
2167298A  10/1985  United Kingdom .

OTHER PUBLICATIONS

Chem Abst. 110: 111342 Mar. 1989.
Chem Abst. 107: 88954, Sep. 1987.

*Primary Examiner*—Gregory Hook
*Attorney, Agent, or Firm*—Scully, Scott, Murphy & Presser

[57] ABSTRACT

A method of preventing or alleviating tissue damage, diabetes and complications thereof, bone disorders, disorders related to transplantation, disorders related to abnormal levels of lipoproteins, cardiovascular disease and inflammatory disorders by providing a mammal having one or more of the above diseases with a preventing or an alleviating effective amount of a compound having the formula $C_6H_6(OH)_{6-n}(OPO_3H_2)_n$, where n is an integer of 1 or 2.

6 Claims, No Drawings

USE OF MONO AND DI INOSITOLPHOSPHATES FOR TREATING INFLAMMATION

The present invention relates to the use of a compound of formula (I):

$$C_6H_6(OH)_{6-n}(OPO_3H_2)_n \quad (I)$$

n=1 or 2 for the preparing of a medicament for preventing, alleviating or combatting different conditions in mammals including man.

The invention also relates to a pharmaceutical composition comprising as a pharmaceutically active ingredient a specific compound of formula (I).

Inositolphosphates are a group of compounds occuring in different plants, as constituents in cell membranes, etc. The hexaphosphorylated myo-inositol, phytic acid, is present in different grains at varying amounts. It is known that lower inositol phosphate derivatives are formed when the grains are germinated. The end products are inositol and inorganic phosphate.

Some other inositolphosphates exist in the blood of birds, especially the inositol-pentaphosphate. This compound regulates the affinity for oxygen to hemoglobin in the erythrocytes.

Lower inositolphosphates linked to glycerol moities are constituents of plasma membranes in cells.

This is valid for very specific isomers of inositoltrisphosphates, inositol-bisphosphates and inositol-monophosphates. These inositolphosphates are released within the cells and regulate different metabolic pathways.

From C. A., vol. 33 (1939), abstr. no. 7351, no ¾, the use of phosphates including inositolphosphates as an antirachitic diet has been reported. No reference is made to specific inositolphosphates.

The U.S. Pat. No. 4,473,563 discloses the extra corporal treatment of erythrocytes to incorporate therein inositolphosphates to improve the oxygen supply. Then erythrocytes are separated from the blood, which has been pumped out of the body for that purpose. After complicated treatment of erythrocytes the latter are reintroduced into the blood. There is no disclosure of administering inositol phosphates directly to the body.

In the U.S. Pat. No. 2,723,938 the use of inositolphosphates is disclosed for stabilizing dispersions of an aqueous suspension of penicillin. This ensures that brief simple manual shaking will restore a state of complete and uniform dispersion of the penicillin after prolonged storage.

From the European Patent No. 179.439 a pharmaceutical composition comprising as a pharmaceutically active ingredient at least one isomer of inositol-trisphosphate is known. In said patent the effect of this pharmaceutical composition is shown for different areas such as platelet aggregation.

The invention relates to the use of a compound of formula (I) for the preparing of a medicament for preventing, alleviating or combatting for example the following conditions: Tissue damage such as oedema formation, vascular leakage, burns, thiniris and asthma; diabetes or complications thereof such as cataract formation, retinopathy, neuropathy, nephropathy, vascular complications, hyperglycemia and hyperketonemia; bone disorders such as osteoporosis, Paget's disease, bone erosion, hypercalcemia and osteoarthritis; disorders related to transplantation and graft operations such as rejection; abnormal immunological response; abnormal levels of lipoproteins; cardiovascular diseases; hemorrhage and inflammatory conditions such as rheumatoid arthritis and gout.

The inventions also covers the use of a compound of formula (I) for the preparing of a medicament for preventing, alleviating or combatting damage to cell membranes, metal intoxication, conditions of ischemia and reperfusion, conditions of shock, conditions related to vasculitis, dermatitis, gastrointestinal diseases such as ulcerative colitis and pancreatitis, synovitis, periodontal diseases and cerebral diseases, autoimmune diseases such as multiple sclerosis, eye diseases or damage to the retina or lens, light and oxygen induced diseases or damages and skin damages.

The different isomers of the compound of formula (I) are inositol-monophosphates and inositol-bisphosphates. In one preferred embodiment of the invention the inositol-isomer is myo-inositol but also other inositols, i.e. allo-inositol, epi-inositol, chiro-inositol, muco-inositol, cis-inositol, neo-inositol, scyllo-inositol are to be contemplated to be in the scope of the invention.

The different compounds of formula (I) can be produced by degradation of inositol-phosphates containing more than two phosphate groups/inositol molecule followed by separation and purification. The different isomers could also be produced by synthetic methods, chemically or enzymatically, starting with e.g. inositol and a phosphorus source. Furthermore the use of microbiological methods and hybrid-DNA-techniques are also suitable.

The compound of formula (I) can also exist in salt form or as a mixture of salt and acid. Preferably the salt is a salt of sodium, potassium, calcium, magnesium or zinc or a mixture of two or more thereof.

It is suitable that the medicament used according to the invention exists in unit dosage form. Tablets, granules or capsules are suitable administration forms for such unit dosage. These forms can easily be modified in order to provide controlled absorption of the compound in the intestine.

A common pharmaceutically acceptable additive, excipient and carrier can be included in the medicament. The tablets or granules can also contain a disintegrant, which causes the tablets or granules to disintegrate in the intestine. Other administration forms are e.g. slow release or transdermal administration, nasal, rectal, intra-articular, topical, intraperitoneal and subcutaneous administration. In certain cases, especially in acute situations, it is preferable to use the unit dosage in the form of a solution for intravenous administration.

The medicament according to the present invention can preferably also contain another pharmaceutically active ingredient in addition to the compound of formula (I). The amount of the compound of formula (I) is in the range of 5% to 95% especially 15% to 95% by weight of the pharmaceutically active ingredients.

The medicament is preferably containing 0.01 g to 1.5 g of the compound of formula (I).

For administration to human patients appropriate dosages can routinely be determined by those skilled in this art by the extension of the results obtained in animals at various dosages.

The preferred dosage for humans falls within the range of 0.1 mg to 1000 mg, especially 0.1 mg to 200 mg of the compound of formula (I)/day/kg body weight.

The compound of formula (I) exist in cyclic forms. In order to better describe specific compounds of formula (I) used in preferred embodiments of the invention the following formula (II) is used:

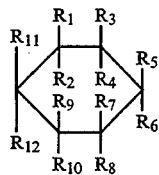
(II)

In preferred embodiments of the invention the compounds of formula (II) is selected from the group where:

$R_3$ is phosphate, $R_1$, $R_5$, $R_8$, $R_9$, $R_{12}$ are hydroxyl and $R_2$, $R_4$, $R_6$, $R_7$, $R_{10}$, $R_{11}$ are hydrogen.

$R_3$ and one of $R_1$, $R_5$, $R_8$, $R_9$, $R_{12}$ are phosphate, the remaining are hydroxyl and $R_2$, $R_4$, $R_6$, $R_7$, $R_{10}$, $R_{11}$ are hydrogen.

$R_1$ is phosphate, $R_3$, $R_5$, $R_7$, $R_{10}$, $R_{11}$ are hydroxyl $R_2$, $R_4$, $R_6$, $R_8$, $R_9$, $R_{12}$ are hydrogen.

$R_5$ is phosphate, $R_1$, $R_3$, $R_7$, $R_{10}$, $R_{11}$ are hydroxyl $R_2$, $R_4$, $R_6$, $R_8$, $R_9$, $R_{12}$ are hydrogen.

$R_1$ and one of $R_3$, $R_5$, $R_7$, $R_{10}$, $R_{11}$ are phosphate, the remaining are hydroxyl and $R_2$, $R_4$, $R_6$, $R_8$, $R_9$, $R_{12}$ are hydrogen.

$R_5$ and one of $R_3$, $R_7$, $R_{10}$, $R_{11}$ are phosphate, the remaining and $R_1$ are hydroxyl and $R_2$, $R_4$, $R_6$, $R_8$, $R_9$, $R_{12}$ are hydrogen.

$R_1$ is phosphate, $R_3$, $R_6$, $R_7$ $R_9$, $R_{12}$ are hydroxyl and $R_2$, $R_4$, $R_5$, $R_8$, $R_{10}$, $R_{11}$ are hydrogen.

$R_9$ is phosphate, $R_1$, $R_3$, $R_6$, $R_7$ and $R_{12}$ are hydroxyl and $R_2$, $R_4$, $R_5$, $R_8$, $R_{10}$, $R_{11}$ are hydrogen.

$R_{12}$ is phosphate, $R_1$, $R_3$, $R_6$, $R_7$ $R_9$ are hydroxyl and $R_2$, $R_4$, $R_5$, $R_8$, $R_{10}$, $R_{11}$ are hydrogen.

$R_1$ and one of $R_3$, $R_6$, $R_7$ $R_9$, $R_{12}$ are phosphate, the remaining are hydroxyl and $R_2$, $R_4$, $R_5$, $R_8$, $R_{10}$, $R_{11}$ are hydrogen.

$R_9$ and one of $R_3$, $R_6$, $R_7$, $R_{12}$ are phosphate, the remaining and $R_1$ are hydroxyl and $R_2$, $R_4$, $R_5$, $R_8$, $R_{10}$, $R_{11}$ are hydrogen.

$R_{12}$ and one of $R_3$, $R_6$, $R_7$ are phosphate, the remaining and $R_1$, $R_9$ are hydroxyl and $R_2$, $R_4$, $R_5$, $R_8$, $R_{10}$, $R_{11}$ are hydrogen.

$R_3$ is phosphate, $R_1$, $R_5$, $R_8$, $R_{10}$, $R_{12}$ are hydroxyl and $R_2$, $R_4$, $R_6$, $R_7$, $R_9$, $R_{11}$ are hydrogen.

$R_{10}$ is phosphate, $R_1$, $R_3$, $R_5$, $R_8$, $R_{12}$ are hydroxyl and $R_2$, $R_4$, $R_6$, $R_7$, $R_9$, $R_{11}$ are hydrogen.

$R_3$ and one of $R_1$, $R_5$, $R_8$, $R_{10}$, $R_{12}$ are phosphate, the remaining are hydroxyl and $R_2$, $R_4$, $R_6$, $R_7$, $R_9$, $R_{11}$ are hydrogen.

$R_{10}$ and one of $R_1$, $R_5$, $R_8$, $R_{12}$ are phosphate, the remaining and $R_3$ are hydroxyl and $R_2$, $R_4$, $R_6$, $R_7$, $R_9$, $R_{11}$ are hydrogen.

$R_3$ is phosphate, $R_1$, $R_6$, $R_8$, $R_9$, $R_{12}$ are hydroxyl and $R_2$, $R_4$, $R_5$, $R_7$, $R_{10}$, $R_{11}$ are hydrogen.

$R_6$ is phosphate, $R_1$, $R_3$, $R_8$, $R_9$, $R_{12}$ are hydroxyl and $R_2$, $R_4$, $R_5$, $R_7$, $R_{10}$, $R_{11}$ are hydrogen.

$R_3$ and one of $R_1$, $R_6$, $R_8$, $R_9$, $R_{12}$ are phosphate, the remaining are hydroxyl and $R_2$, $R_4$, $R_5$, $R_7$, $R_{10}$, $R_{11}$ are hydrogen.

$R_6$ and one of $R_1$, $R_8$, $R_9$, $R_{12}$ are phosphate, the remaining and $R_3$ are hydroxyl and $R_2$, $R_4$, $R_5$, $R_7$, $R_{10}$, $R_{11}$ are hydrogen.

$R_1$ is phosphate, $R_3$, $R_6$, $R_7$, $R_{10}$, $R_{12}$ are hydroxyl and $R_2$, $R_4$, $R_5$, $R_8$, $R_9$, $R_{11}$ are hydrogen.

$R_{12}$ is phosphate, $R_1$, $R_3$, $R_6$, $R_7$, $R_{10}$ are hydroxyl and $R_2$, $R_4$, $R_5$, $R_8$, $R_9$ $R_{11}$ are hydrogen.

$R_1$ and one of $R_3$, $R_6$, $R_7$, $R_{10}$, $R_{12}$ are phosphate, the remaining are hydroxyl and $R_2$, $R_4$, $R_5$, $R_8$, $R_9$, $R_{11}$ are hydrogen.

$R_{12}$ and one of $R_3$, $R_6$, $R_7$, $R_{10}$ are phosphate, the remaining and $R_1$ are hydroxyl and $R_2$, $R_4$, $R_5$, $R_8$, $R_9$, $R_{11}$ are hydrogen.

$R_1$ is phosphate, $R_3$, $R_5$, $R_8$, $R_{10}$, $R_{11}$ are hydroxyl and $R_2$, $R_4$, $R_6$, $R_7$, $R_9$, $R_{12}$ are hydrogen.

$R_5$ is phosphate, $R_1$, $R_3$, $R_8$, $R_{10}$, $R_{11}$ are hydroxyl and $R_2$, $R_4$, $R_6$, $R_7$, $R_9$, $R_{12}$ are hydrogen.

$R_8$ is phosphate, $R_1$, $R_3$, $R_5$, $R_{10}$, $R_{11}$ are hydroxyl and $R_2$, $R_4$, $R_6$, $R_7$, $R_9$, $R_{12}$ are hydrogen.

$R_1$ and one of $R_3$, $R_5$, $R_8$, $R_{10}$, $R_{11}$ are phosphate, the remaining are hydroxyl and $R_2$, $R_4$, $R_6$, $R_7$, $R_9$, $R_{12}$ are hydrogen.

$R_5$ and one of $R_3$, $R_8$, $R_{10}$, $R_{11}$ are phosphate, the remaining and $R_1$ are hydroxyl and $R_2$, $R_4$, $R_6$, $R_7$, $R_9$, $R_{12}$ are hydrogen.

$R_8$ and one of $R_3$, $R_{10}$, $R_{11}$ are phosphate, the remaining and $R_1$, $R_5$ are hydroxyl and $R_2$, $R_4$, $R_6$, $R_7$, $R_9$, $R_{12}$ are hydrogen.

$R_1$ is phosphate, $R_3$, $R_5$, $R_7$, $R_9$, $R_{11}$ are hydroxyl and $R_2$, $R_4$, $R_6$, $R_8$, $R_{10}$, $R_{12}$ are hydrogen.

$R_5$ is phosphate, $R_1$, $R_3$, $R_7$ $R_9$ and $R_{11}$ are hydroxyl and $R_2$, $R_4$, $R_6$, $R_8$, $R_{10}$, $R_{12}$ are hydrogen.

$R_9$ is phosphate, $R_1$, $R_3$, $R_5$, $R_7$, $R_{11}$ are hydroxyl and $R_2$, $R_4$, $R_6$, $R_8$, $R_{10}$, $R_{12}$ are hydrogen.

$R_1$ and one of $R_3$, $R_5$, $R_7$, $R_9$, $R_{11}$ are phosphate, the remaining are hydroxyl and $R_2$, $R_4$, $R_6$, $R_8$, $R_{10}$, $R_{12}$ are hydrogen.

$R_5$ and one of $R_3$, $R_7$, $R_9$, $R_{11}$ are phosphate, the remaining and $R_1$ are hydroxyl and $R_2$, $R_4$, $R_6$, $R_8$, $R_{10}$, $R_{12}$ are hydrogen.

$R_9$ and one of $R_3$, $R_7$, $R_{11}$ are phosphate, the remaining and $R_1$, $R_5$ are hydroxyl and $R_2$, $R_4$, $R_6$, $R_8$, $R_{10}$, $R_{12}$ are hydrogen.

One of $R_1$, $R_4$, $R_5$, $R_8$, $R_9$, $R_{12}$ is phosphate, the remaining hydroxyl and $R_2$, $R_3$, $R_6$, $R_7$, $R_{10}$, $R_{11}$ are hydrogen.

Two of $R_1$, $R_4$, $R_5$, $R_8$, $R_9$, $R_{12}$ are phosphate, the remaining hydroxyl and $R_2$, $R_3$, $R_6$, $R_7$, $R_{10}$, $R_{11}$ are hydrogen.

The function of the medicament is to reverse, prevent or alleviate damage to membranes of different cell types but especially cell membranes of platelets, erythrocytes, leucocytes such as white blood cells and endothelial cells. The use of the medicament results in an improved stabilization, a decreased deformation and an improved function of the different cells. Other results of the use of the medicament are regulation of membrane fluidity, the incorporation of cell membrane components such as cholesterol and the production, incorporation and balance between different phospholipids.

Furthermore the function of the medicament is to reverse, prevent or alleviate specific types of cell to cell attachment, which are deleterious to the body. For example leucocytes, a group of cells with diverse functions, are activated under some physiological and pathological conditions and adhere to other cell types such as endothelial cells. The adhesion process leads to different forms of cytotoxicity, phagocytosis, chemotaxis and induction of cell proliferation and differentiation. The events often leads to conditions described above such as tissue damage, cardiovascular diseases and other types of diseases.

The cell to cell adhesion process is regulated by specific types of receptors. The mode of action of the medicament is to regulate the receptor function with primarily and antagonistic effect by the compound of formula (I).

The above mentioned processes often involve cell damage and cell destruction caused by certain enzymes such as hydrolases, proteases and the alike. Many of these enzymes, for example lysosomal enzymes, are activated via processes involving receptor interactions. The medicament also interacts with these type of receptors with a beneficial regulation as a consequence.

The invention also relates to a pharmaceutical composition comprising as a pharmaceutically active ingredient a specific compound of formula (I) or a salt thereof and a pharmaceutically acceptable carrier, excipient or additive therefore.

The specific compound of formula (I) is selected from the group consisting of: epi-inositol-monophosphate, epi-inositol-bisphosphate, muco-inositol-monophosphate, muco-inositol-bisphosphate, neo-inositol-monophosphate, neo-inositol-bisphosphate, chiro-inositol-monophosphate, chiro-inositol-bisphosphate, allo-inositol-monophosphate, allo-inositol-bisphosphate, cis-inositol-monophosphate, cis-inositol-bisphosphate, scyllo-inositol-monophosphate or scyllo-inositol-bisphosphate.

The invention is further explained below in connection with embodiment examples of which Example 1 shows the production of myo-inositol-monophosphate. Example 2 and 3 teach the production of a solution of a sodium salt of myo-inositol-monophosphate and tablets of a calcium salt of myo-inositol-bisphosphate, respectively.

EXAMPLE 1

A 1.2 gram quantity of the sodium salt of myo-inositol-1.2.3-trisphosphate was dissolved in 900 ml sodium acetate buffer pH 4.6.

50 gram of baker's yeast was added with stirring and incubation was continued at 45° C. for 90 mins. The hydrolysis was then stopped by adding 30 ml of ammonia to pH 12. The suspension was centrifuged and the supernatant was collected.

500 ml of the supernatant was passed through an ion-exchange column (Dowex 1, chloride form, 25 mm×250 mm) and eluted with a linear gradient of sodium chloride (0 to 0.5M NaCl) at pH 12.

Aliquots of eluted fractions were completely hydrolyzed in order to determine the contents of phosphorus and inositol. The peaks correspond to different inositolphosphates and the largest peak with a phosphorus-/inositol ratio of one was further investigated with NMR.

Structural determination showed the product to be myo-inositol-2-monophosphate.

EXAMPLE 2

0.5 gram of a sodium salt of inositol-monophosphate and 0.77 gram NaCl were dissolved in 98.73 ml of water for injection to form a solution suitable for injection into a person or an animal.

EXAMPLE 3

Tablets of the calcium salt of D-myo-inositol-1.2-bisphosphate ($IP_2$) were produced in the following way.

50 gram calcium salt of $IP_2$, 132 gram lactose and 6 gram acacia were mixed. Purified water was then added to the mixture, whereupon the mixing was continued until a suitable consistency was obtained. The mixture was sieved and dried. Then the mixture was blended with 10 gram talcum and 2 gram magnesium stearate. The mixture was compressed into tablets each weighing 200 mg.

We claim:

1. A method of treating an inflammatory disorder in a human or an animal comprising administering to a human or an animal in need thereof an inflammatory disorder pharmaceutically effective amount of at least one isomer of an inositol monophosphate, inositol diphosphate or a salt thereof.

2. A method in accordance with claim 1 wherein said isomer is provided as a salt of an anion selected from the group consisting of sodium, potassium, calcium, magnesium, zinc and mixtures thereof.

3. A method in accordance with claim 1 wherein said inositol monophosphate or said inositol diphosphate is provided in a concentration in the range of between about 5% and about 95% by weight, based on the total weight of said pharmaceutically active ingredient.

4. A method in accordance with claim 2 wherein said salt is provided with a pharmaceutically acceptable carrier, excipient or additive.

5. A method in accordance with claim 4 wherein said salt and said pharmaceutically acceptable carrier, excipient or additive are provided in the form of tablets, granules or solutions.

6. A method in accordance with claim 1 wherein said isomer is selected from the group consisting of myo-inositol-monophosphate, myo-inositol-bisphosphate, epi-inositol-monophosphate, epi-inositol-bisphosphate, muco-inositol-monophosphate, muco-inositol-bisphosphate, neo-inositol-monophosphate, neo-inositol-bisphosphate, chiro-inositol-monophosphate, chiro-inositol-bisphosphate, allo-inositol-monophosphate, allo-inositol-bisphosphate, cis-inositol-monophosphate, cis-inositol-bisphosphate, scyllo-inositol-monophosphate and scyllo-inositol-bisphosphate.

* * * * *